(12) United States Patent
Benedict et al.

(10) Patent No.: US 7,045,349 B2
(45) Date of Patent: May 16, 2006

(54) METHOD OF ISLET ISOLATION USING PROCESS CONTROL

(76) Inventors: Daniel J. Benedict, 3037 S. Princeton Ave., 3R, Chicago, IL (US) 60616; Lorna S. Mosse, 3037 S. Princeton Ave., 3R, Chicago, IL (US) 60616

( * ) Notice: Subject to any disclaimer, the term of this patent is extended or adjusted under 35 U.S.C. 154(b) by 160 days.

(21) Appl. No.: 10/056,662

(22) Filed: Jan. 23, 2002

(65) Prior Publication Data

US 2002/0132341 A1 Sep. 19, 2002

Related U.S. Application Data

(60) Provisional application No. 60/263,273, filed on Jan. 23, 2001.

(51) Int. Cl.
*C12N 5/00* (2006.01)
(52) U.S. Cl. .................... 435/325; 435/286.1; 435/366; 435/375; 435/378; 435/379; 435/380; 435/381
(58) Field of Classification Search ................ 435/325, 435/378, 286.1, 379, 380, 381, 366, 375
See application file for complete search history.

(56) References Cited

U.S. PATENT DOCUMENTS

| | | | |
|---|---|---|---|
| 4,868,121 A | 9/1989 | Scharp et al. | ................ 435/268 |
| 5,079,160 A | 1/1992 | Lacy et al. | ............... 435/240.2 |
| 5,273,904 A * | 12/1993 | Langley | .................... 435/283.1 |
| 5,322,790 A | 6/1994 | Scharp | |
| 5,424,209 A * | 6/1995 | Kearney | .................. 435/286.5 |
| 5,612,188 A * | 3/1997 | Shuler et al. | .................. 435/29 |
| 5,834,005 A | 11/1998 | Usala | |
| 5,837,738 A | 11/1998 | Williamson | |
| 5,853,976 A | 12/1998 | Hesse | |
| 5,879,939 A | 3/1999 | Gray | |
| 5,919,703 A * | 7/1999 | Mullen et al. | ............... 435/381 |
| 5,919,775 A | 7/1999 | Amin | |
| 5,952,215 A | 9/1999 | Dwulet et al. | .............. 435/220 |

OTHER PUBLICATIONS

Bond, M.D. and Van Wart, H.E., "Purification and Separation of Individual Collagenases of *Clostridium histolyticum* Using Red Dye Ligand Chromatography," *Biochemistry* 1984; 23:3077-3085.
Bond, M.D. and Van Wart, H.E., "Characterization of the Individual Collagenases from *Clostridium histolyticum,* " *Biochemistry* 1984; 23:3085-3091.

Scharp, D.W., "Isolation and Transplantation of Islet Tissue," *World Journal of Surgery* 1984; 8:143-151.
Eckhardt, T., Jahr, H., Federlin, K. and Bretzel, R.G., "Endotoxin impairs the engraftment of rat islets transplanted beneath the kidney capsule of C57BL/6-mice," *Journal of Molecular Medicine* 1999; 77:123-125.
Jahr, H., Pfeiffer, G., Hering, B.J., Federlin, K., and Bretzel, R.G., "Endotoxin-mediated activation of cytokine production in human PBMCs by collagenase and Ficoll," *Journal of Molecular Medicine* 1999; 77:118-120.
Linetsky, E., Inverardi, L., Kenyon, N.S., Alejandro, R., and Ricordi, C., "Endotoxin Contamination of Reagents Used During Isolation and Purification of Human Pancreatic Islets," *Transplantation Proceedings* 1998; 30:345-346.
Smith, Jr., G.N., Brandt, K.D., and Hasty, K.A., "Procollagenase Is Reduced to Inactive Fragments upon Activation in the Presence of Doxycycline," *Annals New York Academy of Sciences* 1994; 732:436-438.
Vargas, F., Vives-Pi, M., Somoza, N., Armengol, P., Alcade, L., Marti, M., Costa, M., Serradell, L., Dominguea, O., Fernandez-Llamazares, J., Julian, J.F., Sanmarti, A., and Pujol-Borrell, R., "Endotoxin Contamination May Be Responsible for the Unexplained Failure of Human Pancreatic Islet Transplantation," *Transplantation* 1998; 65(5):722-727.
Scharp—World J. of Surgery—8:143-151 (1984).
Bond—Biochemistry—23:3085-3091 (1984).
Jahr—J. of Mol. Med. 77:(1):110-120 (1984).
Vargas—Trans. 65:(5):722-727 (1999).
Linetsky—Trans. Process—30:345-346 (1998).
Eckhardt J. of Mol Med (Berlin) 77(1):123-125 (1998).
Smith—Anals on N.Y. Acad Sci. 732:436-438 (1999).
Bond—Biochemistry 23:3077 (1984).

* cited by examiner

*Primary Examiner*—Leon B. Lankford, Jr.
(74) *Attorney, Agent, or Firm*—Robert M. Hunter (57) ABSTRACT

Advanced Islet Separation Technology incorporates an automated method, automated control methodology, process control interface, and automated apparatus to separate (isolate) and process pancreatic islets in a tissue suspension in physiological process solution, utilizing microprocessor controllers and computer control and software programming to interface and control the process temperature, process flowrate, percent hydrogen concentration, dissolved oxygen concentration, endotoxin concentration, dissolved nitric oxide concentration, nitric oxide synthase concentration, proteolytic enzyme activity, and pressure of the islet containing physiological process solution, including real-time process data acquisition and recording of the process variables.

50 Claims, 5 Drawing Sheets

AUTOMATED ISLET SEPARATION APPARATUS PROCESS CONTROL VALVE LOGIC

401

| ACTION | STATE | VALVE |
|---|---|---|
| FILL | OPEN | 104 116 132 139 154 180 |
| | CLOSED | 115 117 125 127 131 135 137 153 |
| CIRCULATE AND RINSE | OPEN | 116 126 132 139 153 180 |
| | CLOSED | 104 115 117 125 127 131 135 137 154 |
| DRAIN | OPEN | 104 116 126 132 139 153 154 180 |
| | CLOSED | 115 117 125 127 131 135 137 |
| REFILL | OPEN | 115 125 126 132 137 180 |
| | CLOSED | 104 116 117 127 131 135 139 153 154 |
| PANCREAS ADDITION IN DYNAMIC FLOW DIGESTION CHAMBER | OPEN | 115 125 126 132 139 153 |
| | CLOSED | 104 116 117 127 131 135 137 154 |
| DIGESTION, SEPARATION AND CIRCULATION WITH DYNAMIC FLOW DIGESTION CHAMBER FORWARD FLOW | OPEN | 116 126 132 139 153 180 |
| | CLOSED | 104 115 117 125 127 131 135 137 154 |
| DIGESTION, SEPARATION AND CIRCULATION WITH DYNAMIC FLOW DIGESTION CHAMBER REVERSE FLOW | OPEN | 115 117 125 127 132 139 153 180 |
| | CLOSED | 104 116 126 131 135 137 154 |
| AUTOSAMPLE AND CIRCULATE | OPEN | 116 126 132 135 139 153 180 |
| | CLOSED | 104 116 118 126 128 132 137 154 |
| DILUTE AND COLLECT | OPEN | 104 115 116 117 126 131 132 135 137 139 153 154 |
| | CLOSED | |
| OXYGEN SPARGING ON | OPEN | 146 |
| OXYGEN SPARGING OFF | CLOSED | 146 |
| HELIUM SPARGING ON | OPEN | 149 |
| HELIUM SPARGING OFF | CLOSED | 149 |

METHOD OF ISLET ISOLATION USING PROCESS CONTROL

CROSS-REFERENCE TO RELATED APPLICATIONS

This application claims the benefit of U.S. Provisional Application No. 60/263,273, filed Jan. 23, 2001.

Automated method, automated process control methodology, process control interface, and automated apparatus for pancreatic islet isolation (separation) and processing utilizing microprocessor controllers and computer control of the process variables and automated apparatus including real-time process data acquisition.

STATEMENT REGARDING FEDERALLY SPONSORED RESEARCH OR DEVELOPMENT

"Not Applicable"

REFERENCE TO A MICROFICHE APPENDIX

"Not Applicable"

FIELD OF THE INVENTION

The present invention relates to the isolation of pancreatic islets for transplantation into diabetic patients. The invention presents Advanced Islet Separation Technology, an automated method of islet isolation (separation), automated process control methodology, process control interface, and automated apparatus to separate and process pancreatic islets in physiologic process solution utilizing microprocessor control and computer control of the process variables and automated apparatus. The invention may be uniformly applied to islets harvested from animals and mammals either transgenic or non-transgenic.

BACKGROUND OF THE INVENTION

The islets of Langerhans, endocrine tissue containing insulin producing beta cells, represent about one to two percent of the total mass of the human pancreas. Separation or isolation of the islets from the connective matrix and remaining exocrine tissue is advantageous and beneficial for laboratory experimentation and transplantation purposes. Islet transplantation is a most promising and minimally physiologically invasive procedure for treatment of type I diabetes mellitus. Transplanting islets rather than complete pancreatic tissue has the distinct advantages of ease of transplantation, and the elimination of the pancreatic exocrine function of the donor tissue involving secretion of digestive enzymes. Liberating islets from pancreatic exocrine tissue is the initial and crucial step that influences islet transplantations. The important objective in islet isolations is to provide sufficient numbers of viable functional and potent islets for transplantation.

Early methods of islet separation involved chopped pancreatic fragments mixed with collagenase and incubated around 37 degrees C, D. Scharp, World Journal of Surgery 8:143–151, 1984, incorporated herein by reference. Collagenase breaks down and digests pancreatic tissue, freeing islets, however, prolonged exposure to proteolytic enzymatic digestion destroys the initially separated islets. If the separation is stopped to protect the early released islets, too few islets are freed from the surrounding exocrine tissue. Islet isolation in small mammals was improved utilizing mechanical distension of the pancreas, increasing islet yield through mechanical separation of pancreatic tissue. Yet, with larger mammals this technique did not allow sufficient numbers of islets to be separated from a single donor for transplantation. Further improvements in islet separation included perfusion of the pancreas with collegenase via ductal distention causing mechanical disruption of exocrine tissue, U.S. Pat. No. 5,322,790, D. Scharp, Jun. 21, 1994, incorporated herein by reference. In addition, tissue disintegration resulting in islet separation by mechanical disruption of the pancreas has been effected by perfusion of the pancreas with an enzyme containing solution while in a chamber with solid spheres and contacting (beating) the pancreas with the spheres, either by hand or by motorized repetitive motion. This is mentioned in U.S. Pat. No. 5,853,976, Hesse, et al., Dec. 29, 1998, incorporated herein by reference, and is a component of the standard isolation technique currently practiced. Recently, islets have been isolated using enzymatic digestion and sound waves to rupture pancreatic tissue, U.S. Pat. No. 5,879,939, Gray et al., Mar. 9, 1999, incorporated herein by reference. Islets have also been separated using both a warm and cold digestion stage, in which physiologic solutions other than Hanks Balanced Salt Solution (HBSS) have been utilized for the second cold digestion stage, with increased islet yield and functionality when compared to the islets separated utilizing HBSS for the second cold separation, U.S. Pat. No. 5,919,703, Mullen, et al., Jul. 6, 1999, incorporated herein by reference.

While larger scale islet separation from human pancreases has become possible with advances in technology, the previously cited techniques fall short in terms of efficiency, and are inadequate for scale up or mass production in which many donor pancreases are processed at different research and transplantation centers, medical facilities, or commercial locations. In consideration of the lack of donor pancreases, current islet isolation techniques are also inadequate to continuously and repetitively batch process porcine pancreases, or pancreases from animals or mammals, transgenic or non-transgenic, to produce islets for xenotransplantation. In the previously referenced techniques and patents there exist limitations in the methodologies that may significantly affect the outcome of the islet separation process.

Collegenases, metalloendoproteinases that cleave collagen into smaller peptide fragments, are zinc-containing enzymes that require divalent calcium as a cofactor for stabilization and optimal activity. Using traditional collegenases detrimentally affects pancreatic digestion due to the impurities present in the collegenase solutions. Traditional collagenase preparations are concentrated from bacterial (*Clostridium histolyticum*) culture supernatants. Roche, a manufacturer of molecular biochemicals, states that such collegenase preparations are heterogeneous, containing as many as 30 different enzymes, pigments, cellular debris, and endotoxins. The most significant liabilities of traditional collegenase are variability and endotoxin levels. In traditional collagenase, the primary enzymatic constituent is collegenase, classes I and II, described by Bond and Van Wart, Biochemistry, 23:3077, 1984, and Biochemistry, 23:3085–3091, 1984, incorporated herein by reference. Other proteases found include neutral protease, clostripain, elastase, trypsin, and aminopeptidase. Non-proteolytic enzymes isolated from collagenase preparations include hyaluronidase, galactosidase, acetyl glucosaminidase, phospholipase, fucosidase, and neuraminidase.

Endotoxin is associated with a number of cellular events including cell activation with subsequent cytokine secretion, and programmed cell death (apoptosis). Endotoxin exposure is postulated to cause a loss of transplanted pancreatic islets, Vargas et al., Transplantation, 65(5): 722–727, Mar. 15, 1998, incorporated herein by reference. They have demonstrated that supernatants generated during islet separation were able to induce certain inflammatory cytokines in the islets during the separation process. They postulate that endotoxins and locally induced cytokines accompanying the transplanted islets activate the endothelium and promote lymphomonocytic infiltration of the transplanted islets and surrounding liver tissue. Jahr et al., J. Mol. Medicine (Berlin), 77(1):118–120, January 1999, incorporated herein by reference, suggest that endotoxin-induced early inflammatory reactions may inhibit the function and survival of isolated cells or cell aggregates after transplantation. Eckhardt et al., J. Mol. Medicine (Berlin), 77(1):123–125, January 1999, incorporated herein by reference, have determined that islet xenograft survival increased in endotoxin free conditions. Clearly, endotoxin and accompanying cellular reactions may cause non-function and rejection of transplanted islets.

Alternatively, Roche manufactures non-traditional purified collegenase blends of collegenase I and II (including either neutral protease dispase or neutral protease thermolysin) for pancreatic tissue dissociation, under the product name of Liberase®. Liberase prepared for human islet separation incorporates thermolysin. Neutral protease acts synergistically with collegenase during intercellular matrix digestion. During Liberase enzyme production, collagenase isoenzymes are purified from raw collagenase by a process that removes greater than 99% of the endotoxin present in the collagenase raw material. Enzyme purification also removes non-enzymatic components and bacterial cellular debris that may be toxic to islets. Collagenases I and II are purified to greater than 95% homogeneity. Roche proof data shows that Liberase contains on average less than 10 Endotoxin Units (EU) per milligram (mg), while traditional collegenase preparations contain far greater than 1000 EU/mg and may have as much as 13000 EU/mg. Liberase represents a defined product for tissue dissociation, U.S. Pat. No. 5,952,215, Dwulet, et al., Sep. 14, 1999, incorporated herein by reference. Linetsky et al., Transplant Proc., 30(2):345–346, March 1998, incorporated herein by reference, demonstrated that the use of Liberase enzyme improved human islet yield, compared with traditional collagenase. Examination of absolute islet number, islet number per gram of pancreas, islet equivalent number, and islet equivalent number per gram of pancreas indicated that Liberase enzyme improved islet yield. Liberase gives maximal tissue dissociation performance with minimal endotoxin complicity when compared with traditional collegenases.

Apoptosis can also be initiated by biochemical factors other than endotoxin. Nitric oxide and its metabolites are known to cause cellular death from nuclear damage (apoptosis), U.S. Pat. No. 5,834,005, A. Usula, Nov. 10, 1998, incorporated herein by reference. Nitric oxide is a recognized multifunctional mediator that is produced by and acts on various cells, and participates in inflammatory and autoimmune-mediated tissue destruction, U.S. Pat. No. 5,919,775, Amin et al., Jul. 6, 1999, incorporated herein by reference. The group of enzymes known as nitric oxide synthases catalyzes nitric oxide production. Nitric oxide synthase (NOS) is expressed in mammalian cells. Utilizing cofactors in the presence of oxygen, it catalyzes the mixed functional oxidation of L-arginine to L-citrulline and nitric oxide, by removing a guanidino nitrogen from L-arginine to form nitric oxide. Interleukin-1 (IL-1) has been shown to induce the expression of the cytokine inducible isoform of nitric oxide synthase in pancreatic islets. The production of nitric oxide has been proposed to be the effector molecule that mediates IL-1's inhibitory effects on islet function, U.S. Pat. No. 5,837,738, Williamson et al, Nov. 17, 1998, herein incorporated by reference.

Yet, the deleterious effects of nitric oxide on islet cells can be alleviated by a variety of means. Inhibitors of nitric oxide synthase have been identified. Nitric oxide synthase (NOS), and subsequently nitric oxide, can be inhibited by derivatives of L-arginine, the natural substrate of nitric oxide synthase. These include methyl-, dimethyl-, or amino-substituted guanidines. These inhibitory compounds are also chemically known as aminoguanidinie, N,N'-diaminoguanidine, methylguanidine and 1,1-dimethylguanidine (U.S. Pat. No. 5,837,738 and U.S. Pat. No. 5,919,775, both previously incorporated herein by reference). Nitric oxide production can also be inhibited by 2,4-diamino-6-hydroxy-pyrimidine, a compound that interferes with the activity of a cofactor of inducible nitric oxide synthase. Antibiotic tetracycline also inhibits nitric oxide synthase, thus preventing the formation of nitric oxide, as do doxycycline, and minocycline, a semisynthetic tetracycline (U.S. Pat. No. 5,919,775, previously incorporated herein by reference). Nitric oxide can also be inhibited by nitric oxide scavengers such as cysteine, and other sulfated compounds such as dextran, heparin, and cystine, U.S. Pat. No. 5,834,005 (previously incorporated herein by reference). Alternatively, sparging with an inert gas such as helium can effectively control and eliminate the dissolved oxygen concentration in the islet containing physiologic process solution, thereby hindering the production of nitric oxide via reduction and catalytic oxidation of L-arginine by NOS and cofactors. In combination with oxygen removal from the process solution, cysteine, dextran, heparin, and cystine also inhibit nitric oxide formation that results from relative states of islet hypoxia. Nitric oxide inhibition and scavenging improves islet survival and secretory function. It is certainly beneficial to control or inhibit the formation of nitric oxide in islets and the islet containing physiologic process solution.

The method of mechanical tissue dissociation with glass marbles, steel balls or other sufficiently dense and solid objects, either by hand or with mechanical shaking (Ricordi shaker), may cause tissue damage and trauma to islets resulting from excessive shear stress during the separation process. While repetitive mechanical agitation and contacting the pancreas with solid objects effects tissue disruption aiding enzymatic digestion, such current practices in standard isolation techniques are subjective, and vary between research facilities and transplantation centers.

Although sonication has been employed to aid pancreatic tissue digestion, one certain limitation in this technique is the 'static' water bath that the 'bagged' pancreas is placed in. Interestingly, this technique is continued until the pancreas appears 'cracked', yet, no mention of the internal temperature of the pancreas is noted. Static digestion by any method offers no means of forced-convective heat transfer to maintain a constant processing temperature (cooling during sonication) of the digesting pancreas or the resulting tissue suspension, by the process solution. It is possible that the internal temperature of a bagged pancreas in such a static system exceeds 37 to 40 degrees C., a temperature considered optimal for functional enzymatic digestion, yet, minimal in thermal shock and deactivation of islets due to elevated temperature. A statically digested pancreas in a bag offers no opportunity to maintain a controlled internal pancreatic temperature. This method presents no opportunity to dilute the tissue suspension, which precludes a real-time method to control, deactivate, or inhibit the digestive enzymes in the processing solution, during islet separation and processing, in the dilution and collection phase.

At the XVIII International Congress of the Transplantation Society, Aug. 27–Sep. 1, 2000 in Rome, Italy, advances in pancreatic islet cell transplantation procedures were reviewed and discussed. Existing limits of transplantation and novel approaches to achieving tolerance were evaluated. It was noted that success of recent transplantations (Edmonton Protocol) might certainly be due to the use of immunosuppression that was not toxic to beta cells. Avoiding the use of corticosteroids, induction therapy with anti-IL-2 antibody, and low-dose tacrolimus and sirolimus maintenance were undoubtedly key factors in non-rejection and continued islet tolerance. The quality of the purified islets also contributed to the success of the transplantations, yet, acquired by tedious and laborious manual methods lacking in process control methodology and neglecting important process variables. Current challenges were also assessed, specifically, the standardization of islet separation technology, and the need to development a standardized, reproducible, and automated method to separate and produce high-quality islet cells.

Presently there exists no process control methodology of the islet separation process that takes into account crucial process variables that may be controlled to optimize islet isolation while standardizing and automating the islet separation process. Importantly, there are separation and processing variables that have been neglected and omitted which compromise the reproducibility and repeatability of the islet separation process from location to location. Objectively applying advanced process control methodology and automating the islet isolation process with process control technology can optimize the islet separation process.

BRIEF SUMMARY OF THE INVENTION

The present invention relates to the application of advanced control methodology and process control technology, incorporating an automated method of islet separation (isolation) and processing utilizing microprocessor and computer control and software programming, to control the process variables and interface the process control methodology to the automated islet separation apparatus, via an electrical (electronic) interface and a graphic user interface, and includes real-time data acquisition (DAQ) and recording of the process variables. Process variables that influence the islet separation process have been identified and incorporated into the automated method of islet separation by integrating automated control of the process variables through the process control interface to the islet separation apparatus, utilizing an analog and digital (A/D) electrical (electronic) interface with feedback from and control of the islet separation apparatus. The identified process variables that influence the islet separation process are the process solution, the process temperature (T), the process flowrate (F), the percent hydrogen (pH), the dissolved oxygen (DO) concentration, the dissolved nitric oxide (NO) concentration, the dissolved carbon dioxide (CO2) concentration, the digestive enzyme (PE) activity, the endotoxin (E) concentration, the antibiotic (A) concentration, and the pressure (P) of the islet containing physiologic process solution. By controlling the variables that influence the reproducibility and repeatability of the islet separation process, the present invention is superior to the currently employed and subjectively standard islet isolation techniques, which neglect process control of the important and essential process variables.

In the preferred application of the automated method of islet separation utilizing the automated islet separation apparatus, a single researcher performs the islet isolations. Once a pancreas is suitable prepared and made ready for islet separation processing (U.S. Pat. No. 5,322,790, U.S. Pat. No. 5,853,976, both previously incorporated herein by reference), the researcher uses the automated islet separation method to start the automated islet separation apparatus with a single command via the electrical (electronic) and graphic user interface, initiating the fill, circulate and rinse cycle. After the initial rinse cycle and the rinse solution is discarded, the islet separation apparatus again fills with physiologic solution and the method and apparatus will then pause in operation and wait for the pancreas to be loaded in the dynamic flow digestion chamber.

After pancreas addition, once the dynamic flow digestion chamber is sealed, the researcher restarts the automated method of islet separation and the automated islet separation apparatus with a single command via the graphic user interface, and monitors the process via the electrical (electronic) and graphic user interface (computer display). Once the automated islet separation method and the islet separation apparatus are restarted, the islet separation apparatus will automatically adjust, attain, maintain, regulate, and control the desired, preset, and programmed values of the process variables during the digestion, separation, and circulation phase. The process variables are the programmed (setpoint) process temperature (T), the programmed (setpoint) process flowrate (F), the programmed (setpoint) percent hydrogen (pH), the programmed (setpoint) dissolved oxygen (DO) concentration, the dissolved nitric oxide (NO) concentration, the dissolved carbon dioxide (CO2) concentration, the programmed (setpoint) digestive enzyme (PE) activity, the endotoxin (E) concentration, the antibiotic (A) concentration, and the pressure (P) of the islet containing physiologic process solution.

At the end of the digestion, separation, and circulation phase of islet processing, when the desired extent of islet separation is achieved, a single command from the researcher cycles the automated islet separation apparatus into the dilution and collection phase. During the dilution and collection phase, methodology is employed to control, deactivate, and inhibit the digestive effects of proteolytic enzymes and tissue dissociating agent collegenase (Liberase), protecting the islets from unnecessary degradation during dilution and collection. Quite simply, during dilution and collection, collegenase can be inhibited by the addition of chelators of divalent cations such as citrate, EDTA, or EGTA. Metalloendoproteinase activity can also be inhibited by cysteine, tetracycline, and doxycycline, Smith Jr. et al, Annals NY Acad Sci 732:436–438, 1994, incorporated herein by reference. Throughout the dilution and collection phase, the fundamental process variables are still controlled at the programmed (setpoint) values. During this phase of islet processing, the islet separation apparatus will dilute and autocollect the islet containing physiologic process solution via the automated islet autocollector.

The researcher may at any time alter, control, stop, and restart the process, when necessary, due to unforeseen disturbances. While the islet separation process is fully automated, it is still an automated batch process fully under the researcher's control via the electrical (electronic) and graphic user interface. Ultimately, the process will need no manual intervention and the entire separation process, after the loading of the pancreas into the dynamic flow digestion chamber, will proceed by the automated method. The automated method of islet separation, the automated islet separation apparatus, and the process variables are microprocessor and computer controlled, and the entire islet separation process starting with the fill, circulate and rinse cycle, the pancreas addition proceeding through digestion, separation and circulation, and ending with the dilution and collection phase may be accomplished with either start stop commands to process controllers and pumps and or three single keystrokes or mouse clicks, or touch screen commands.

During automated islet separation processing, specifically digestion, separation and circulation, the islet containing physiologic process solution is monitored via autosampled aliquots of the process solution. Depending on the level of sophistication required by the individual researcher, research facility, or transplantation center, the extent of pancreatic digestion and islet separation monitored in real-time may be accomplished either manually via autosampled aliquots, staining, and image analysis software, or automated on-line via integration of a flow through sample cell, autosampling, staining, and image analysis software. Importantly, during the islet separation, the endotoxin concentration of the islet containing physiologic process solution is monitored, recorded and controlled in real-time via the same autosampled aliquot.

Process control and data acquisition of the automated method of islet separation and the automated islet separation apparatus is accomplished with microprocessor controllers and a windows based (Win98) microprocessor computer (PC) operating in the LabView graphical software-programming environment (G), for example. The microprocessor computer (PC) is equipped with analog and digital solid-state electrical (electronic) input output control boards that are electrically (electronically) interfaced to various analog and digital input output control hardware via sensors and electrical (electronic) connections. Islet separation process data are collected in real-time and the researcher is presented with an electrical (electronic) and graphical interface that contains an interactive process flowsheet displaying system status and processing data, which accepts user input and feedback to the process. Pumps, valves, thermocouples, sensors, probes, and transducers may be located on a graphical process flowsheet (computer display) and correspond to their actual physical location on the automated islet separation apparatus. The software may be programmed to automatically control the automated islet separation apparatus and the process variables at the programmed set points; yet, the researcher may at any time manually override the process. Islet separation process data are acquired during islet isolation from the process sensors and process controllers and microprocessor computer (PC) and logged in a data file for post-processing analysis, quality assurance, validation, and regulatory purposes.

Analog output process sensors including thermocouples, dissolved oxygen sensor, percent hydrogen probe (sensor), nitric oxide sensor, carbon dioxide sensor, endotoxin sensor, process pump tachometer (flowrate), and pressure (transducer) sensor are interfaced to signal conditioning input modules which input process data through the electrical (electronic) interface to the microprocessor controllers and the microprocessor computer (PC). The process pump speed (flowrate) is controlled by analog output from the microprocessor computer (PC) through a signal conditioning output module and the electrical (electronic) interface. The process temperature (T), the process flowrate (F), the percent hydrogen (pH) concentration, the dissolved oxygen (DO) concentration, the dissolved nitric oxide (NO) concentration, the endotoxin (E) concentration, the proteolytic enzyme (PE) activity, the antibiotic (A) concentration, and the pressure (P) are controlled by feedback from process sensors and analog and digital output from the microprocessor controllers and the microprocessor computer (PC) via analog and digital and solid state relays (SSR) through the electrical (electronic) interface. Analog and digital output from the microprocessor computer (PC) via the analog-digital (A/D) interface through the electrical (electronic) interface is used to activate electric solenoid valves controlling the process solution flow and flow direction. The process solution flow and direction of fluid flow of the automated islet isolation apparatus may be operated under manual and or electrical control via the electrical (electronic) and graphical interface.

Other operating systems such as WinXP, Win2000, WinNT, Win95, Win3.1, Linux, Warp, OS-2, or Mac OS for example, and other software-programming environments, Fortran, Pascal, C, C+, C++, Basic, Visual Basic, Java, HTML, or VRML for example, as well as programmable logic controllers (PLC) and or programmable microprocessors (non PC) may be utilized to interface the automated control methodology and automated islet separation apparatus. Microprocessor controllers and or microprocessor computer (PC) and or programmable logic controller (PLC) may also be employed for automating the motion control of the autosampler, autocollector, and dynamic flow digestion chamber. General-purpose input output boards (GPIB) or RS-232 (RS 485) inputs and outputs may also be employed to control the operation of the automated islet separation apparatus including data acquisition.

It is the object of this invention to present Advanced Islet Separation Technology and apply the technology to pancreatic islet separation (isolation) and processing. Advanced Islet Separation Technology incorporates advanced control methodologies to control and monitor the critical process variables that affect the reproducibility and repeatability of islet separation processes from location to location.

Specifically, the present invention utilizes process control methodology and applies it to pancreatic islet isolation, uniquely incorporating an automated method, automated control methodology, process control interface, and an automated apparatus to separate and process pancreatic islets in physiologic process solution.

More particularly, this invention utilizes process variable setpoints employing microprocessor controllers, and microprocessor computer control and software programming (code), to automate and interface the process control methodology, on-line in real-time, to control the process temperature (T), the process flowrate (F), the percent hydrogen (pH) concentration, the dissolved oxygen (DO) concentration, the dissolved nitric oxide (NO) concentration, the dissolved carbon dioxide ($CO_2$) concentration, the digestive (proteolytic) enzyme (PE) activity, the endotoxin (E) concentration, the antibiotic (A) concentration, and the pressure (P) of the islet containing physiologic process solution during islet separation and processing, via an analog and digital electrical (electronic) interface, with feedback from the process sensors and control of the automated islet separation apparatus by the microprocessor controllers and computer and software code.

This invention provides on-line in real-time, process data acquisition and recording of the process variables during islet separation and processing, via an analog and digital electrical (electronic) interface and input from the process sensors in the islet separation apparatus.

This invention incorporates real-time image analysis to determine the extent of pancreatic digestion and islet separation to control the digestion time, utilizing image analysis software. Real-time image analysis may be accomplished either by discrete autosampling and manually staining utilizing microscopy and image analysis, or automated via a flow through sample cell, and staining utilizing discrete on-line image analysis, via an analog and digital electrical (electronic) interface and input to the islet separation apparatus.

This invention also provides a modified and improved temperature controlled, dynamic flow digestion chamber, incorporating forward fluid flow and reversing fluid flow, and rotary motion (or linear motion, or eccentric motion) with self-contained sonic transducers with sonication applied to the dynamically flowing islet containing processing fluid, to aid tissue digestion via an analog and digital electrical (electronic) interface and input to the islet separation apparatus (dynamic flow digestion chamber).

Provided by this invention are methods to control, deactivate, and inhibit the digestive effects of the proteolytic enzymes utilized to digest pancreatic connective tissue (collagen) at the end of the digestion, separation and circulation phase, during the dilution and collection phase.

This invention further provides a method to control and monitor in real-time, the nitric oxide concentration present in the islet containing physiologic process solution during islet separation and processing.

This invention further provides a method to monitor and control in real-time via discrete analysis, the endotoxin concentration present in the islet containing physiologic process solution during islet separation and processing.

This invention further provides a method to monitor and control in real-time, the carbon dioxide concentration present in the islet containing physiologic process solution during islet separation and processing.

The above is a brief description of the advantages of the present invention. The features, embodiments, and advantages of the invention will be apparent to those skilled in the science from the accompanying drawings, following description, and appended claims.

DETAILED DESCRIPTION OF THE INVENTION

The invention is directed at an improved and automated method of islet isolation (separation), employing automated process control methodology, a process control interface, and automated apparatus to separate and process pancreatic islets in physiologic process solution utilizing microprocessor controllers and microprocessor computer control (PC) of the process variable setpoints and automated apparatus, including real-time process data acquisition. The invention is also directed at a dynamic flow digestion chamber incorporating forward fluid flow and reversing fluid flow, rotary motion (or linear motion, or eccentric motion) with self-contained sonic transducers incorporated in the dynamic flow digestion chamber with sonication applied to the dynamically flowing islet containing processing solution.

Figure 1:
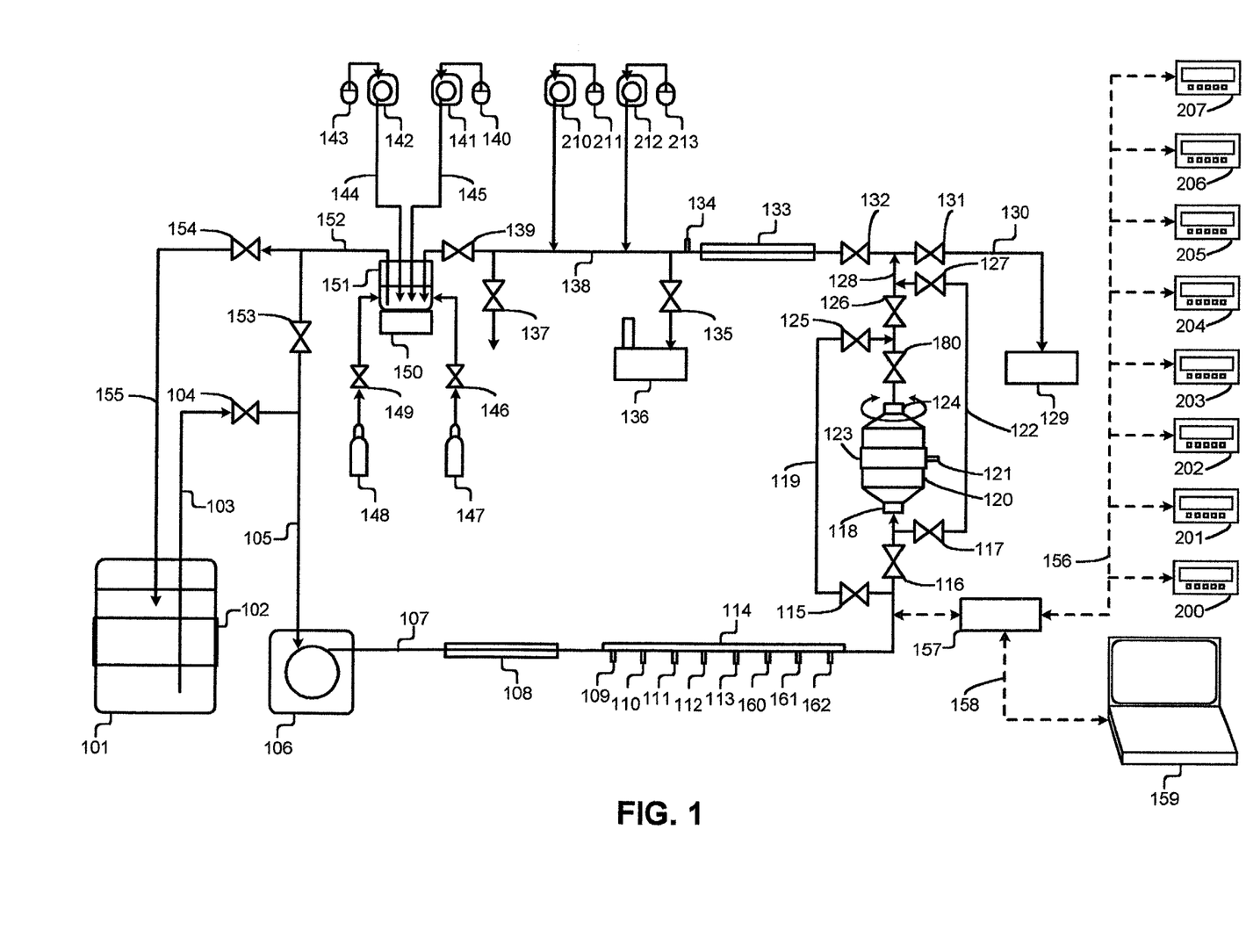
FIG. 1 is a process flowsheet of the automated islet separation apparatus showing the various components of the automated islet separation apparatus and the microprocessor controllers and microprocessor computer interfaced to the automated apparatus according to one preferred embodiment of the invention.

FIG. 1 illustrates a flowchart of the interaction of the various components of the automated islet isolation apparatus according to one preferred embodiment of the invention. As shown in FIG. 1, the physiologic process solution flows from feed tank 101 incorporating heater 102 through process tube 103 through process valve 104 through process tube 105 through process pump 106 through process tube 107 through process heat exchanger 108 through sensor block 114 that contains process sensors 109 dissolved oxygen sensor, 110 nitric oxide sensor, 111 pB sensor, 112 temperature (thermocouple) sensor, 113 pressure (transducer) sensor, 160 endotoxin sensor, 161 carbon dioxide sensor, and in the forward flow direction through process valve 116 through rotary coupling 118 through the dynamic flow digestion chamber 120 incorporating temperature (thermocouple) sensor 121 and process heater 123 through rotary coupling 124 through process valve 180 through process valve 126 through process tube 128 through process valve 132 through process heat exchanger 133 through temperature (thermocouple) sensor 134 through process tube 138 through process valve 139 into collection vessel 151 on stirring plate 150 through process tube 152 through process valve 154 through process tube 155 returning to the feed tank 101 during the circulation and rinse phase of islet processing. After pancreas addition to the dynamic flow digestion chamber, during the digestion, separation, and circulation phase of islet processing the physiologic process solution flows from process tube 152 through process valve 153 again through process tube 105 forming a process loop.

FIG. 1 also illustrates according to one preferred embodiment of the invention the process sensors (previously described) and the microprocessor controllers (setpoint enabled), 200 temperature controller, 201 pH controller, 202 dissolved oxygen controller, 203 endotoxin neutralizing protein (ENP) controller, 204 proteolytic enzyme (collegenase) neutralization (PEN) controller, 205 nitric oxide controller, and 206 carbon dioxide meter, interconnected by electrical (electronic) wiring 156, the analog and digital and connector block interface 157, and microprocessor computer 159 utilizing 157 interconnected by electrical (electronic) wiring 158, the oxygen control valve 146, the oxygen tank 147, the helium tank 148, the helium control valve 149, the acid reservoir 140, the acid pump 141, the acid addition tube 145, the base pump 142, the base reservoir 143, the base addition tube 144, the endotoxin neutralizing protein (ENP) pump 210, the ENP solution reservoir 211, the ENP addition tube 214, the (digestive) proteolytic enzyme neutralization (PEN) pump 212, and the PEN solution reservoir 213, the PEN addition tube 215, which are employed to control the chemical character of the process solution at the setpoints during islet isolation and separation processing. Periodic sampling of the process solution is accomplished via sampling process valve 135 and the auto-sampler 136. When the pancreas has been sufficiently digested, auto-collection of the islets and the process solution is accomplished when process solution flows through process valve 131 through process tube 130 and into the auto-collector 129.

Figure 2:
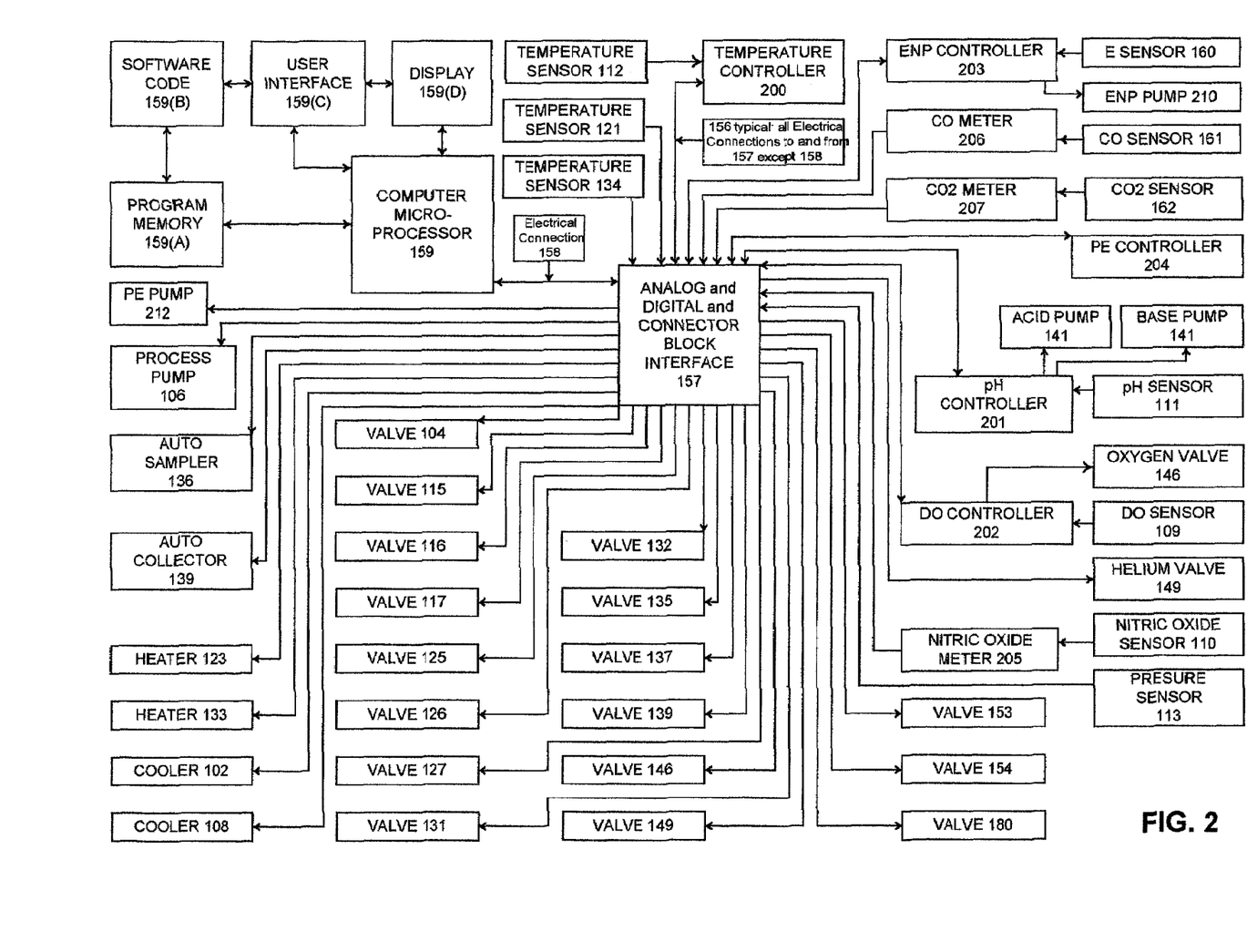
FIG. 2 is a schematic and block diagram of the automated islet separation apparatus showing the interaction of the components of the automated apparatus including the analog and digital electrical (electronic) interface and the microprocessor controllers and the microprocessor computer according to one preferred embodiment of the invention.

FIG. 2 illustrates a schematic and block diagram of the interaction of the various components of the automated islet isolation apparatus, electrical connections and wiring according to one preferred embodiment of the invention. Electrical process connections 156 interface the process sensors 109, 110, 111, 112, 113, 121, 134, 160, 161 (previously described in FIG. 1), the microprocessor process controllers 200, 201, 202, 203, 204, 205 (previously described in FIG. 1), and the microprocessor process meter 206, (previously described in FIG. 1) through the analog and digital and connector block interface 157 to the automated islet separation apparatus. A microprocessor computer (PC) 159 is employed to control the electric (solenoid) process valves 104, 115, 116, 117, 125, 126, 127, 131, 132, 135, 137, 139, 146, 149, 153, 154, 180 (previously described in FIG. 1) and to record the processing data via real-time process data acquisition (DAQ—sensor output from the sensors and microprocessor process controllers and microprocessor process meters) through electrical (electronic) process connections 158 and the analog and digital and connector block interface 157 incorporating input modules. The microprocessor computer 159 consists of the program memory 159 (A) random access memory (RAM) and read only memory (ROM), stored by a hard-drive (HD) and or erasable programmable read only memory (EPROM), software code 159(B) stored by either RAM, ROM, EPROM, or HD, and user interface 159(C) incorporating keyboard, mouse, interconnection cables and a numerical (electrical [electronic]) and graphical display (computer monitor) 159(D).

Figure 3:
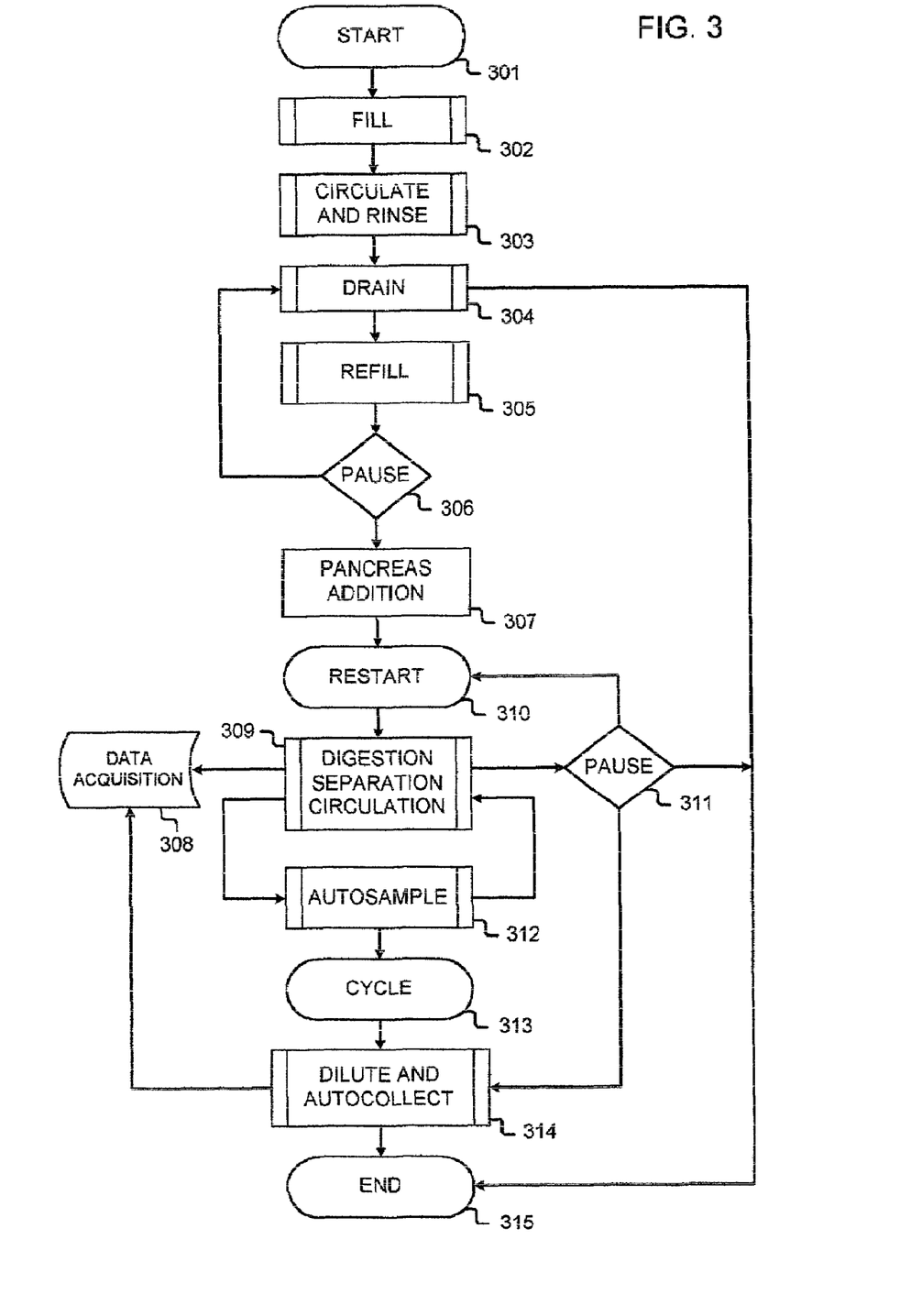
FIG. 3 is a flowchart showing the sequence of operations of the automated islet separation method in the order performed by the automated islet separation apparatus according to one preferred embodiment of the invention.

FIG. 3 illustrates a flowchart illustrating the automated method of islet isolation according to one preferred embodiment of the invention. Initially the automated islet isolation process is started 301, the automated islet separation apparatus fills with physiologic process solution 302, the process solution is circulated and the interior of the islet separation apparatus is rinsed 303, the process solution is drained 304, and the apparatus is refilled 305 with fresh physiologic process solution after which the automated method and automated apparatus pause in operation (flow) 306 while pancreas addition 307 to the digestion chamber takes place. The method and apparatus are restarted 310, initiating pancreatic digestion, separation and circulation 309 of islets and processing fluid, while real-tine process data acquisition (DAQ) 308 is executed. During 309, autosampling 312 is executed and the method and apparatus may be paused 311 at any time. When sufficient numbers of islets have been liberated and separated from the pancreas into the processing solution, the method and apparatus are cycled 313, so dilution and auto-collection 314 are executed and when complete, islet processing ends 315.

Figure 4:
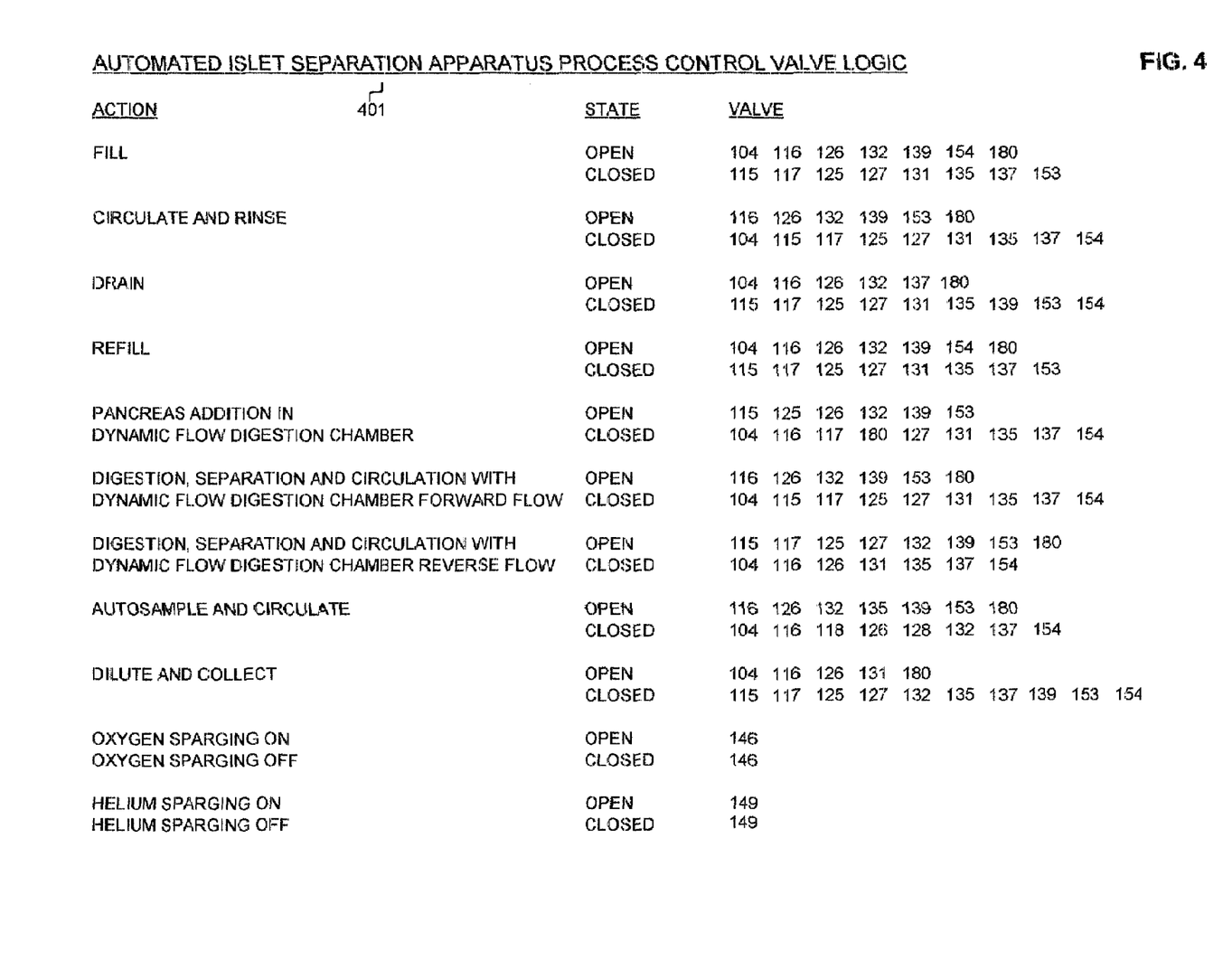
FIG. 4 is a process control valve logic diagram of the automated islet separation apparatus showing the valve logic of the automated method according to one preferred embodiment of the invention.

FIG. 4 illustrates the automated islet separation apparatus process control valve logic 401 for the automated islet separation method and automated islet separation apparatus according to one preferred embodiment of the invention. After the automated method is started 301 (previously described in FIG. 3), the islet isolation apparatus initially fills 302 with physiologic process solution while process valves 104, 116, 126, 132, 154, and 180 are open and process valves 115, 117, 125, 127, 131, 135, 137 and 153 are closed. During the circulation and rinse phase 303 of islet processing, process valves 116, 180, 126, 132, 139, and 153 are open and process valves 104, 115, 117, 125, 127, 131, 135, 137, and 154 are closed. When the process solution is drained 304 from the apparatus process valves 104, 116, 180, 126, 132, and 137 are open and process valves 115, 117, 125, 127, 131, 135, 139, 153 and 154 are closed. The apparatus is refilled 305 with physiologic process solution with process valves 104, 116, 180, 126, 132, and 154 open and process valves 115, 117, 125, 127, 131, 135, 137 and 153 closed. Pancreas addition 307 to the dynamic flow digestion chamber 120 is accomplished while process valves 115, 125, 126, 132, 139 and 153 are open and process valves 104, 116, 117, 180, 127, 131, 135, 137, and 154 are closed. During pancreatic digestion, islet separation, and circulation 308 of the process fluid in the forward direction through the digestion chamber, process valves 116, 180, 126, 132, 139, and 153 are open and process valves 104, 115, 117, 125, 127, 131, 135, 137 and 154 are closed. Throughout pancreatic digestion, islet separation, and circulation 308 of the process fluid in the reverse direction through the digestion chamber, process valves 115, 117, 125, 180, 127, 132, 139, and 153 are open and process valves 104, 116, 126, 131, 135, 137 and 154 are closed. Auto-sampling and circulation 312 of the islet containing process fluid takes place while process valves 116, 180, 126, 132, 135, 139, and 153 are open and process valves 104, 116, 118, 126, 128, 132, 137, and 154 are closed. During dilution and auto-collection process valves 104, 116, 180, 126, and 131, are open and process valves 115, 117, 125, 127, 132, 135, 137, 139, 153, and 154 are closed. Dissolved oxygen is displaced and removed from the process fluid by opening the helium control valve 149 and sparging the process fluid with helium from the helium tank 148. Dissolved oxygen may be added to the process solution by opening the oxygen control valve 146 and sparging the process fluid with oxygen from the oxygen tank 147.

Figure 5:
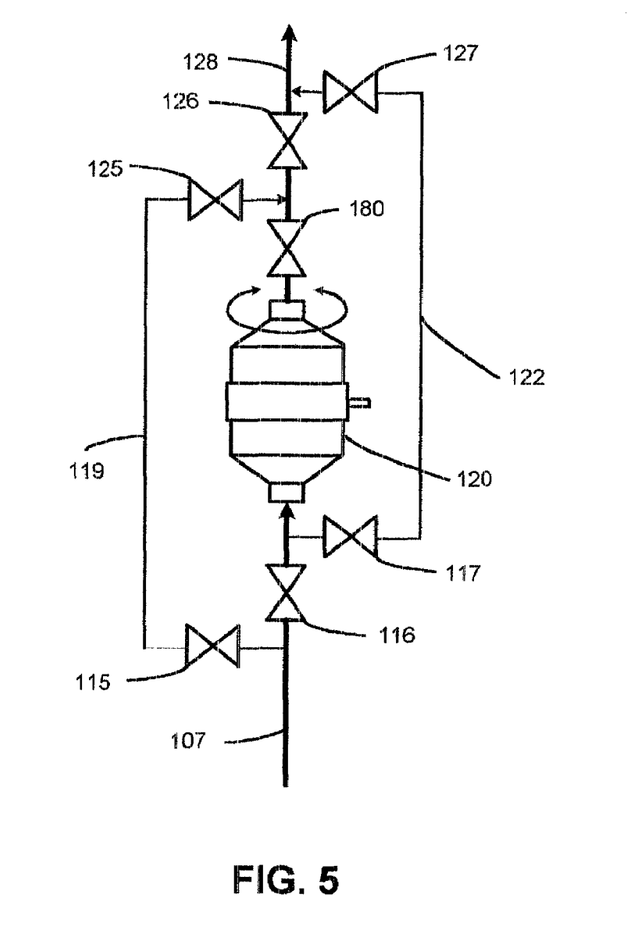
FIG. 5 is a separate view of the dynamic flow digestion chamber showing the direction of forward fluid flow through the digestion chamber according to one preferred embodiment of the invention.

FIG. 5 illustrates the islet containing process solution flow in forward direction through the dynamic flow digestion chamber during pancreatic digestion, islet separation, and process solution circulation 309, (previously described in FIG. 1, FIG. 3, and FIG. 4) according to one preferred embodiment of the invention. The process solution flows through the dynamic flow digestion chamber 120 in the forward direction while process valves 116, 180, and 126 are open and process valves 115, 117, 125, and 127 are closed.

Figure 6:
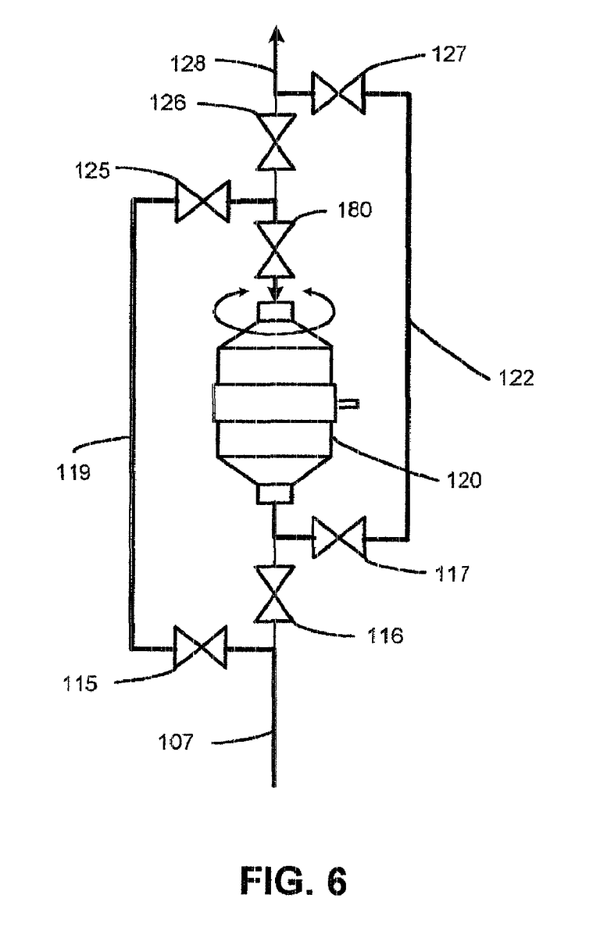
FIG. 6 is a separate view of the dynamic flow digestion chamber showing the direction of reverse fluid flow through the digestion chamber according to one preferred embodiment of the invention.

FIG. 6 illustrates the islet containing process solution flow in reverse direction through the dynamic flow digestion chamber during pancreatic digestion, islet separation, and process solution circulation 309, (previously described in FIG. 1, FIG. 3, and FIG. 4) according to one preferred embodiment of the invention. The process solution flow through the dynamic flow digestion chamber 120 in the reverse direction is achieved while process valves 115, 125, 180, 117, and 127 are open and process valves 116 and 126 are closed.

All publications, patents, and patent documents are incorporated herein by reference, as though individually incorporated by reference. The invention has been described with reference to various specific and preferred embodiments and techniques. However, it should be understood that many variations and modifications might be made while remaining within the spirit and scope of the invention. The above descriptions of exemplary embodiments are for illustrative purposes. Because of variations that will be apparent to those skilled in the science, the present invention is not intended to be limited to the particular embodiments described above. Thus, various modifications of the above-described embodiments will be apparent to those skilled in the art or science. The present invention may also be practiced in the absence of any element not specifically disclosed. The invention may be uniformly applied pancreatic tissue containing islets of Langerhans with insulin producing beta cells harvested from animals and mammals either transgenic or non-transgenic. The scope of the invention is defined by the following claims.

What is claimed is:

1. A method for isolating islets from a portion of a pancreas, comprising:
   introducing the portion of a pancreas to an islet processing solution that contains a digestive enzyme and that is characterized by a plurality of process control variables;
   circulating said islet processing solution around and through the portion of a pancreas and past a plurality of sensors, said plurality of sensors being exposed to said islet processing solution having an output that characterizes a state of one of the process control variables;
   controlling said plurality of process control variables of the islet processing solution during islet isolation with a process controller that is in communication with said plurality of sensors, said process controller having a process control interface and being capable of changing the state of said plurality of process control variables, wherein said plurality of process control variables include a temperature, a flowrate, a pH, a dissolved oxygen concentration, a dissolved nitric oxide concentration, an antibiotic concentration and an endotoxin concentration;
   separating the islets from the portion of pancreas; and
   collecting the separated islets.

2. The method of claim 1, wherein said controlling step comprises controlling said plurality of process control variables with a proportional, integral, derivative controller.

3. The method of claim 1, wherein said controlling step comprises controlling said plurality of process control variables with a microprocessor temperature controller.

4. The method of claim 1, wherein said controlling step comprises controlling said plurality of process control variables with is a microprocessor controller.

5. The method of claim 1, wherein said controlling step comprises controlling said plurality of process control variables with a microprocessor computer.

6. The method of claim 1, wherein said controlling step comprises controlling said plurality of process control variables with a variable resistance transformer.

7. The method of claim 1, wherein the temperature is adjusted by an electrical resistance element in thermal communication with the islet processing solution.

8. The method of claim 1, wherein the temperature is adjusted by steam placed in thermal communication with the islet processing solution.

9. The method of claim 1, wherein the temperature is adjusted by a recirculating fluid bath in thermal communication with the islet processing solution.

10. The method of claim 1, wherein the temperature is adjusted by the ambient temperature of the environment in thermal communication with the islet processing solution.

11. The method of claim 1, wherein the pH is controlled by a microprocessor pH controller between pH 6.00 and pH 8.00.

12. The method of claim 1, wherein the pH is controlled by a microprocessor controller between pH 6.00 and pH 8.00.

13. The method of claim 1, wherein the pH is controlled by a microprocessor computer between pH 6.00 and pH 8.00.

14. The method of claim 1, wherein the pH is controlled by the addition of an acid or base to the islet processing solution.

15. The method of claim 1, wherein the flowrate is controlled by a microprocessor controller between 10.0 milliliters per minute and 4000.0 milliliters per.

16. The method of claim 1, wherein the dissolved oxygen concentration is controlled by a microprocessor controller between 0.000000001 milligrams per milliliter and 10.0 milligrams per milliliter.

17. The method of claim 1, wherein the dissolved oxygen concentration is controlled by sparging the islet processing solution with at least one inert gas selected from the group consisting of helium, neon, argon, krypton and xenon.

18. The method of claim 1, wherein the dissolved nitric oxide concentration is controlled by a microprocessor controller between 0.00000000000001 moles per liter and 1.0 mole per liter.

19. The method of claim 1, wherein the dissolved nitric oxide concentration is controlled by sparging the islet processing solution with at least one inert gas selected from the group consisting of helium, neon, argon, krypton and xenon.

20. The method of claim 1, wherein the endotoxin concentration is controlled by a microprocessor controller between 0.000000001 endotoxin units per milligram and 100.0 endotoxin units per milligram.

21. The method of claim 1, wherein the endotoxin concentration is controlled by the addition of an endotoxin neutralizing protein to the islet processing solution.

22. The method of claim 21 wherein the endotoxin neutralizing protein concentration is controlled by a microprocessor controller between 0.00000000000001 moles per liter and 1.0 moles per liter.

23. The method of claim 1, wherein said plurality of process control the variables further comprise a digestive enzyme activity which is controlled by the addition of one or more antibiotics to the islet processing solution selected from the group consisting of tetracycline, minocycline and doxycycline.

24. The method of claim 1, wherein said plurality of process control the variables further comprise a digestive enzyme activity which is controlled by the addition of one or more chelators of divalent cations to the islet processing solution selected from the group consisting of citrate, EDTA and EGTA.

25. The method of claim 1, wherein said plurality of process control the variables further comprise a digestive enzyme activity which is controlled by the addition of one or more amino acids to the islet processing solution selected from the group consisting of cysteine and cystine.

26. The method of claim 1, wherein said plurality of process control variables further comprise a digestive enzyme activity which is controlled by a microprocessor controller between 0.00000000000001 moles per liter and 1.0 moles per liter.

27. The method of claim 1, wherein the antibiotic concentration is controlled by a microprocessor controller between 0.00000000000001 moles per liter and 1.0 mole per liter.

28. The method of claim 1, wherein said plurality of process control variables further comprise nitric oxide synthase activity which is controlled by the addition to the islet processing solution of one or more derivatives of L-arginine selected from the group consisting of aminoguanidine, N, N'-diaminoguanidine, methylguanidine and 1,1-dimethylguanidine.

29. The method of claim 1, wherein the dissolved nitric oxide concentration is controlled byte addition of 2,4-diamino-6-hydroxy-pyrimidine to the islet processing solution.

30. The method of claim 1, wherein said plurality of process control variables further comprise a pressure which is between 1.0 pound per square inch gauge pressure and 150.0 pounds per square inch gauge pressure.

31. The method of claim 1, wherein said plurality of process control variables comprise a carbon monoxide concentration which is controlled by sparging the islet processing solution with carbon monoxide.

32. The method of claim 1, wherein the pancreas is a human pancreas.

33. The method of claim 1, wherein the pancreas is a transgenic porcine pancreas.

34. The method of claim 1, wherein the pancreas is a non-transgenic porcine pancreas.

35. The method of claim 1, wherein the pancreas is a transgenic mammalian pancreas.

36. The method of claim 1, wherein the pancreas is a non-transgenic mammalian pancreas.

37. The method of claim 1, wherein the pancreas is a transgenic fish pancreas.

38. A method for isolating islets from a pancreatic tissue, comprising:
   a step for introducing the pancreatic tissue to an islet processing solution that contains a digestive enzyme and that is characterized by a plurality of process control variables;
   a step for circulating said islet processing solution through the pancreatic tissue;
   a step for controlling said plurality of process control variables of the islet processing solution during islet isolation, the plurality of process control variables comprising: a temperature, a pH, a flowrate, a dissolved oxygen concentration, a dissolved nitric oxide concentration, a nitric oxide synthase activity, an endotoxin concentration, an endotoxin neutralizing protein concentration, an antibiotic concentration, an amino acid concentration, a dextran concentration, a heparin concentration, and a digestive enzyme activity;
   a step for separating the islets from the pancreatic tissue while the process control variables are controlled; and
   a step for collecting the separated islets.

39. The method claim 38, wherein the digestive enzyme activity is controlled by adding an antibiotic to the islet processing solution.

40. The method claim 38, wherein the digestive enzyme activity is controlled by adding a chelator of divalent cations to the islet processing solution.

41. The method of claim 38, wherein the digestive enzyme activity is controlled by adding an amino acid to the islet processing solution.

42. The method of claim 38, wherein said dissolved nitric oxide concentration is controlled or inhibited by adding to the islet processing solution of one or more derivatives of L-arginine selected from the group consisting of aminoguanidinie, N, N'-diaminoguanidine, methylguanidine, and 1,1-dimethylguanidine.

43. The method of claim 38, wherein said dissolved nitric oxide concentration is controlled or inhibited by adding 2,4-diamino-6-hydroxy-pyrimidine to the islet processing solution.

44. The method of claim 38, wherein said dissolved nitric oxide concentration is controlled or inhibited by adding an amino acid to the islet processing solution.

45. The method of claim 38, wherein said dissolved nitric oxide concentration is controlled or inhibited by adding to the islet processing solution one or more of the compounds selected from the group consisting of dextran and heparin.

46. The method of claim 38, wherein said dissolved nitric oxide concentration is controlled or inhibited by adding to the islet processing solution one or more antibiotics selected from the group consisting of tetracycline, minocycline, and doxycycline.

47. The method of claim 38, wherein the nitric oxide synthase activity is controlled or inhibited by adding to the islet processing solution one or more antibiotics selected from the group consisting of tetracycline, minocycline, and doxycycline.

48. The method of claim 38 wherein:
   said step for controlling one or more of said plurality of process control variables is accomplished with a process controller.

49. The method of claim 38 wherein:
   one or more of said plurality of process control variables is controlled in said step for controlling.

50. The method of claim 38 wherein:
   one or more of said plurality of process control variables is controlled with a process controller in said step for controlling.

* * * * *